(12) United States Patent
Särme et al.

(10) Patent No.: US 7,261,801 B2
(45) Date of Patent: Aug. 28, 2007

(54) METHOD FOR ANALYZING A SAMPLE FROM A PROCESS WITH ON-LINE CAPILLARY ELECTROPHORESIS APPARATUS AND CAPILLARY ELECTROPHORESIS APPARATUS

(75) Inventors: Timo Särme, Espoo (FI); Heli Sirén, Espoo (FI); Rauno Virtanen, Espoo (FI)

(73) Assignee: Valtion teknillinen tutkimuskeskus, VTT (FI)

( * ) Notice: Subject to any disclaimer, the term of this patent is extended or adjusted under 35 U.S.C. 154(b) by 454 days.

(21) Appl. No.: 10/148,957

(22) PCT Filed: Dec. 8, 2000

(86) PCT No.: PCT/FI00/01079

§ 371 (c)(1),
(2), (4) Date: Dec. 9, 2002

(87) PCT Pub. No.: WO01/42777

PCT Pub. Date: Jun. 14, 2001

(65) Prior Publication Data

US 2003/0132113 A1 Jul. 17, 2003

(30) Foreign Application Priority Data

Dec. 8, 1999 (FI) .................................. 19992625
May 2, 2000 (FI) .................................. 20001016

(51) Int. Cl.
*G01N 27/453* (2006.01)
(52) U.S. Cl. ........................ 204/604; 204/601
(58) Field of Classification Search ........ 204/601–604, 204/451–455
See application file for complete search history.

(56) References Cited

U.S. PATENT DOCUMENTS 5,141,621 A    8/1992    Zare et al.
5,496,460 A *   3/1996    Jorgenson et al. .......... 204/604

(Continued)

FOREIGN PATENT DOCUMENTS

EP    0 435 074 A2    7/1991

(Continued)

OTHER PUBLICATIONS

Virtanen, Acta Polytechnica Scandinavica Chemistry Including Metallury Series, No. 123 (1974), pp. 1-67.

(Continued)

*Primary Examiner*—Alex Noguerola
(74) *Attorney, Agent, or Firm*—Birch, Stewart, Kolasch & Birch, LLP

(57) ABSTRACT

Disclosed is a method and apparatus by which a sample can be taken from a process and be analyzed on-line by means of a capillary electrophoresis apparatus. On the feed side of the capillary electrophoresis unit (13) the sample is continuously collected via a duct (16) from the process into the sample feeding system and fed into the capillary ducts (2, 3) through the same duct as is the feed solution, and all the solutions (16, 17, 18, 19) both on the feed side and on the exit end of the capillary electrophoresis unit (13) are pumped through the flow ducts, and the liquids flown through the capillary are removed on the exit end of the capillary electrophoresis unit (13) by means of a liquid treatment system.

19 Claims, 6 Drawing Sheets

Figure 1:
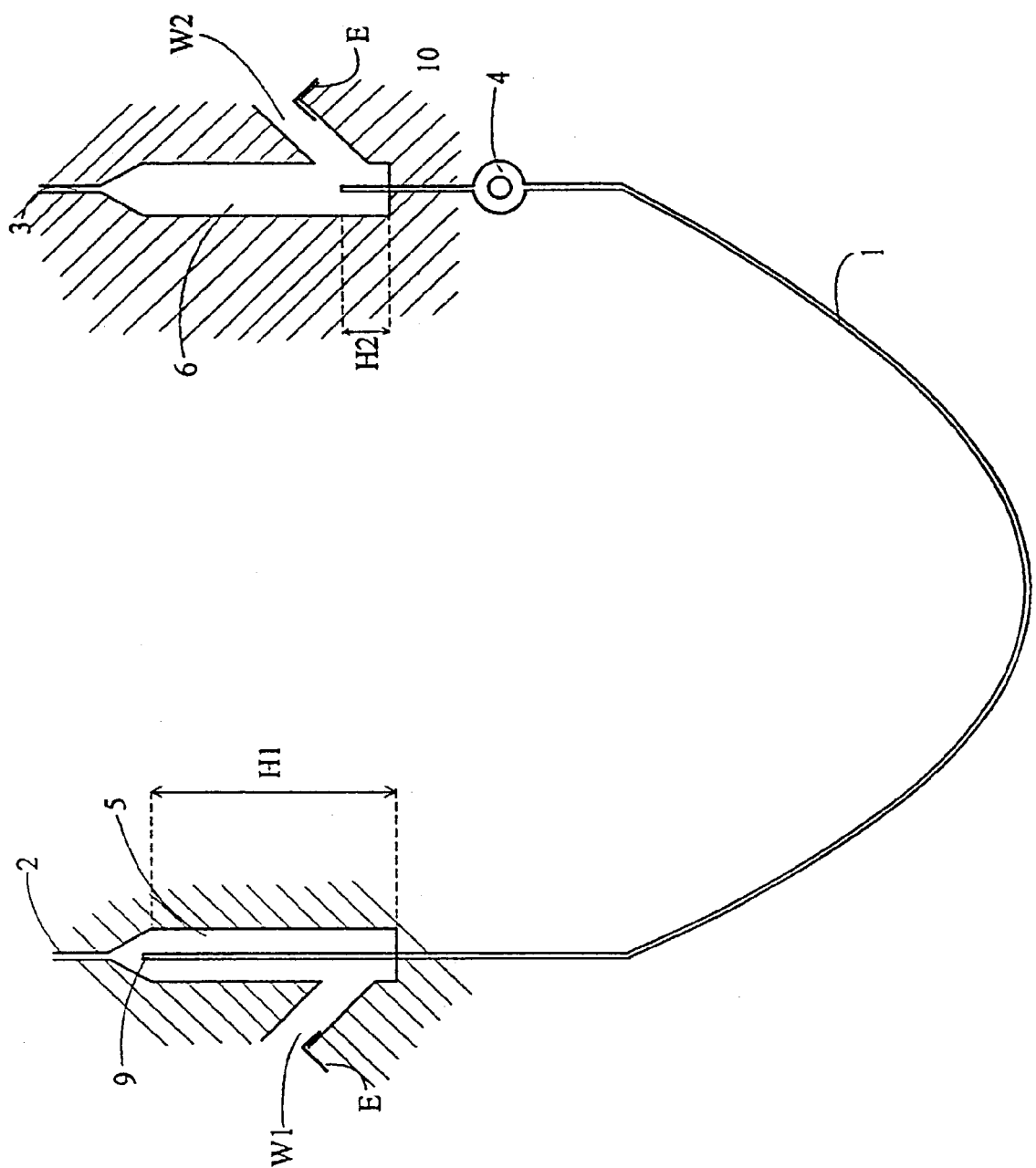

U.S. PATENT DOCUMENTS 5,646,048 A * 7/1997 Templin et al. ............. 436/180
6,190,521 B1   2/2001 Virtanen ..................... 204/453

FOREIGN PATENT DOCUMENTS

EP       0 463859 B1   1/1992
FI         103438 B    4/1999
FI         981054     12/1999
WO      WO99/17111    4/1999

OTHER PUBLICATIONS

Verheggan et al., J. Chromatogr. 452 (1988), pp. 615-622.
Virtanen et al. Suomen Kemistilehti B42 (1969) pp. 182-184.

* cited by examiner

METHOD FOR ANALYZING A SAMPLE FROM A PROCESS WITH ON-LINE CAPILLARY ELECTROPHORESIS APPARATUS AND CAPILLARY ELECTROPHORESIS APPARATUS

This application is the national phase under 35 U.S.C. 371 of Finnish Patent Application No. 19992625, filed Dec. 8,1999, and Finnish Patent Application No. 20001016, filed May 2, 2000.

BACKGROUND OF THE INVENTION

1. Field of the Invention

The invention relates to a method and apparatus by means of which a sample can be taken from a process and be analyzed on-line with a capillary electrophoresis apparatus.

2. Description of the Related Art

Electrophoresis is an electrochemical method by which electrically charged particles, and by certain specialized methods also uncharged particles, in an electrolyte solution can be separated; the sizes of the particles may range from the smallest ions and molecules to colloidal particles. Depending on their electric charges and other properties, particles travel at different velocities in an electric field.

In capillary electrophoresis, the background solution travels in a thin tube, capillary, the viscous forces of the liquid preventing convection. The inner diameter of the capillary is usually between 0.02 and 1 mm. Electrophoresis is thus carried out in a free solution, whereby any interferences caused by a carrier are eliminated. It is also easy to remove from the capillary any thermal energy generated by the electric current, and thus a strong electric field can be used, a factor which speeds up separation. Furthermore, capillary electrophoresis is easy to automate.

In capillary electrophoresis, two vessels containing a background electrolyte solution are connected by a capillary tube containing the same solution. Each vessel is equipped with an electrode. The sample to be analyzed is placed as a short zone at the upstream end of the capillary. In general, for the feeding in of the sample, the end of the capillary is transferred from the background solution vessel to the sample vessel and back. This operation causes interferences and distortions in the background solution in the area of the capillary end and in the sample zone and reduces the precision of the method. It is also necessary to switch off the current for the duration of the transfer of the capillary from one vessel to the other, which may cause changes in the conditions of the run. The same disadvantages are caused if the background solution is changed during a run.

The reactions occurring at the electrodes also change the composition of the solution in the background solution vessels, and these changes may pass into the capillary, causing distortions in the parameters of the test series.

Several researchers have presented apparatus options by means of which the disadvantages stated above can in part be eliminated. Virtanen, Acta Polytechnica Scandinavica, Chemistry Including Metallurgy Series, No. 123 (1974), pp. 1-67, as early as the 1960s used an injection technique that allowed the injection of a sample while the electric current was on. Verheggen et al., J. Chromatogr., 452 (1988), pp. 615-622, and Zare et al., U.S. Pat. No. 5,141,621, have also presented a method for the injection of a sample into a capillary electrophoresis apparatus without switching off the electric current. However, these methods and apparatuses do not provide means for exploiting the numerous possibilities provided by the theoretical uniformity of various electrophoresis applications.

Finnish patent FI 103438 discloses a capillary electrophoresis apparatus wherein the carrying out of a certain electrophoresis application requires the selection of certain initial and limit conditions. The control of the limit conditions in a capillary electrophoresis system means that the composition of the background solution in the vicinity of the capillary ends has to be controlled. According to the patent, this is carried out by continuous pumping of fresh solution past the ends of the separation capillary. Thereby the passing of the reaction products, formed in the electrode reactions, into the capillary is also prevented. In order to avoid a high consumption of the background solution, the volume of the solution ducts has to be minimally small. The design of the apparatus according to the present invention is based on this principle. In the apparatus according to the patent, the test conditions can be selected without limitation, and they can be changed freely during a run. However, this arrangement has the disadvantage that it cannot be linked directly to the process but the feeding in of a sample has to be carried out as a separate function.

SUMMARY OF THE INVENTION

It is an object of the present invention to provide a novel method and apparatus for the feeding of a sample into a capillary electrophoresis apparatus, whereby the abovementioned disadvantages can be eliminated and all the various applications of capillary electrophoresis can easily be carried out using the same apparatus.

The method and apparatus according to the invention are thus suitable for on-line monitoring of various processes. The fields of application that can be mentioned include the food industry, the forest and paper industry, water purification plants, and various processes monitoring the state of the environment. In addition, it is possible to use the method in, for example, nursing and health care. It is clear that the apparatus according to the invention can also be applied in a laboratory, separate from the process.

A special advantage of the invention is the speed and higher reliability of the analyses carried out. Often ions or compounds do not remain in their desired form when a sample is stored or transported; for example, they become oxidized, reduced, hydrolyzed, precipitated, complexed, aggregated, or even completely decomposed. When an on-line method and apparatus are used, such problems will not arise, and thus the results are more reliable and provide a more accurate picture of the real state of the process.

Furthermore, the method and apparatus according to the invention are easy to use and economical, since they require only a small amount of the sample and of various other solutions. For a person skilled in the art it is also clear that it is possible to control the apparatus by computer, in which case it can be used, for example, as a continuous-working analyzer of a process, since it is possible to feed in the sample sequentially, for example, at a feed frequency of 20 seconds. Furthermore, the apparatus according to the invention can be made very small, for example, on a microcircuit, in which case it can be used also in field conditions, for example, for the analysis of water samples.

The method and apparatus according to the invention have the following further advantages:

the capillary electrophoresis technique (isoelectric focusing, electrochemical chromatography of micelles, zone electrophoresis) can be changed in the course of the separation of the analytes;

the solvent can be changed easily and rapidly;

the capillary may also be partly filled with a solid-phase material;

it is possible to reverse the field in the course of the separation of the analytes;

several separation capillaries together can be linked to the apparatus, in which case the sample can be directed to several separation capillaries simultaneously.

BRIEF SUMMARY OF THE DRAWING FIGURES

Figure 2:
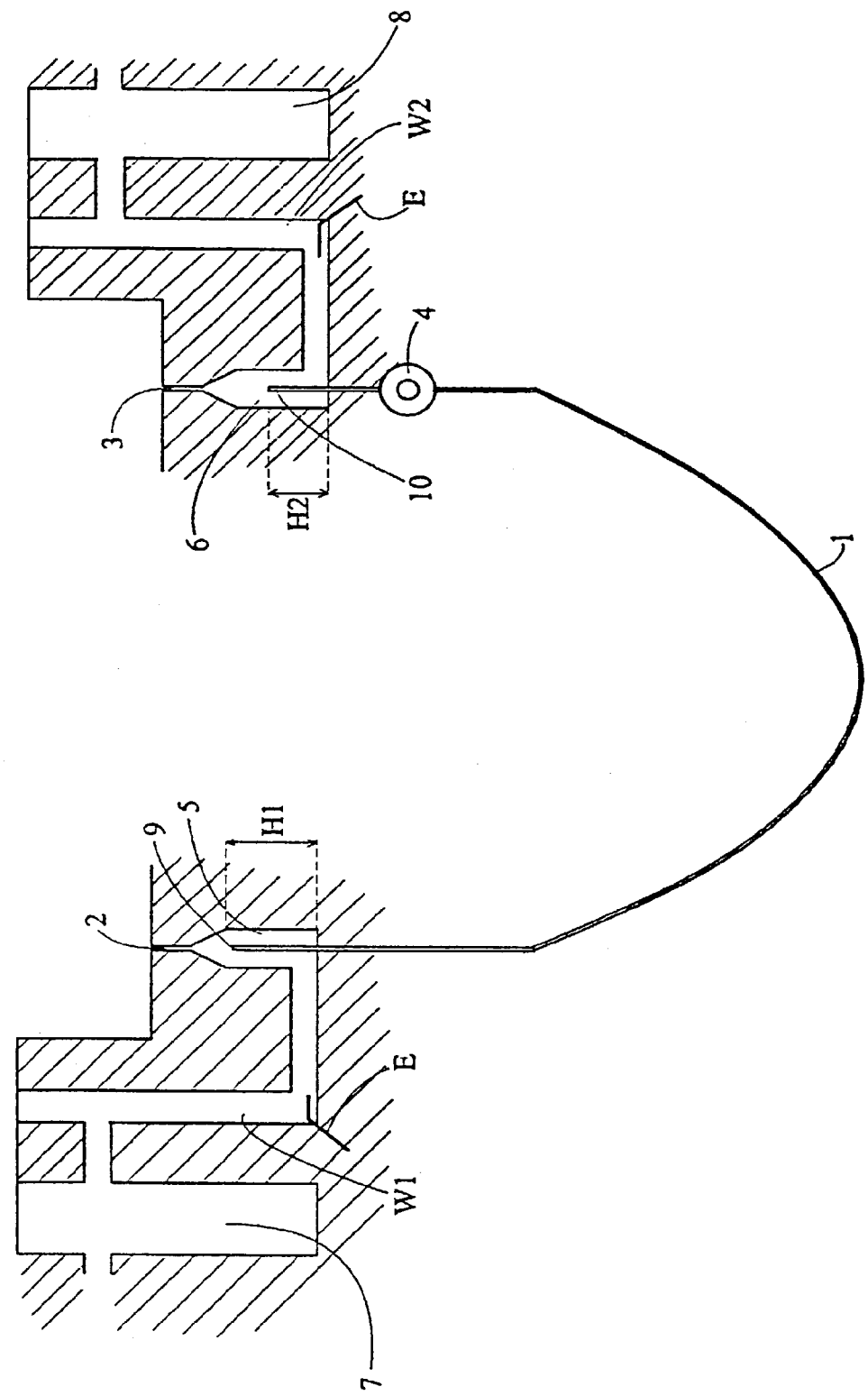
Figure 3A:
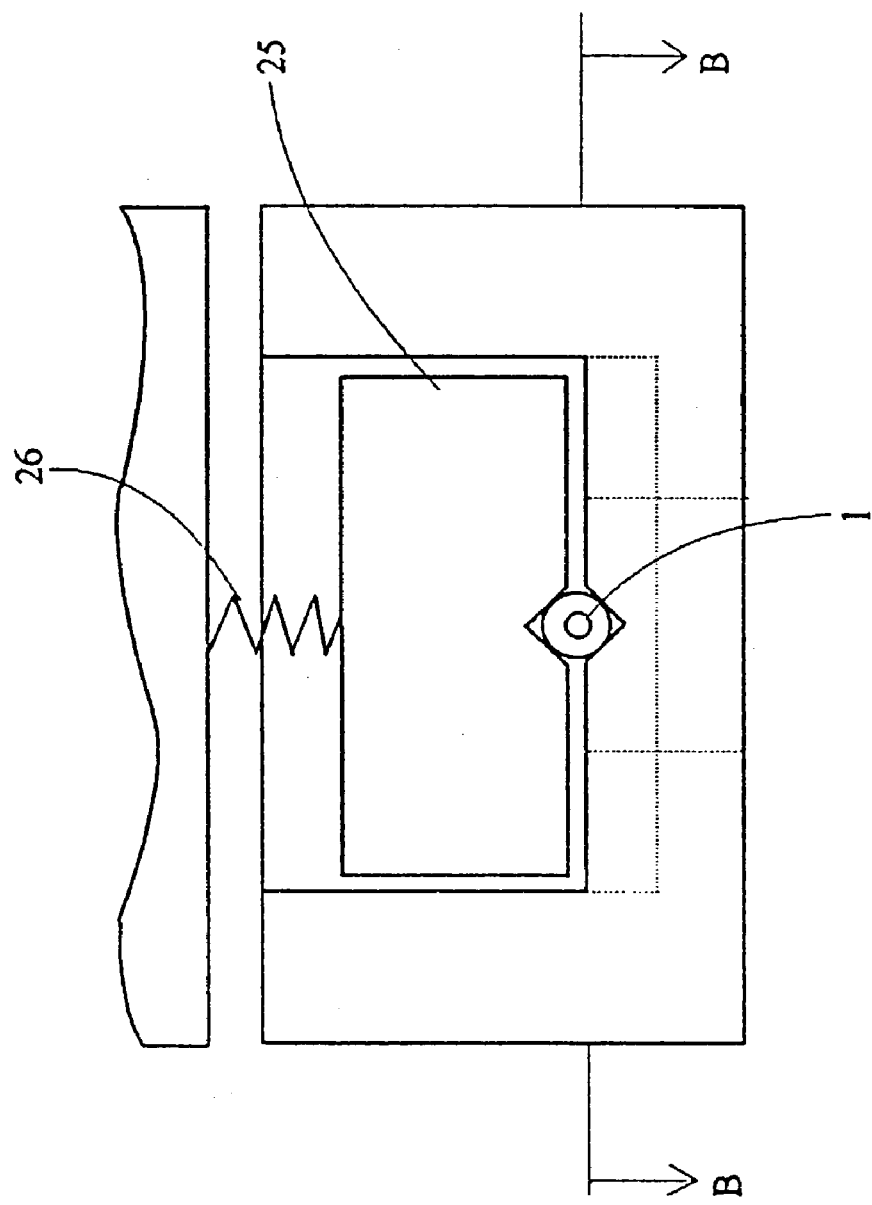
Figure 3B:
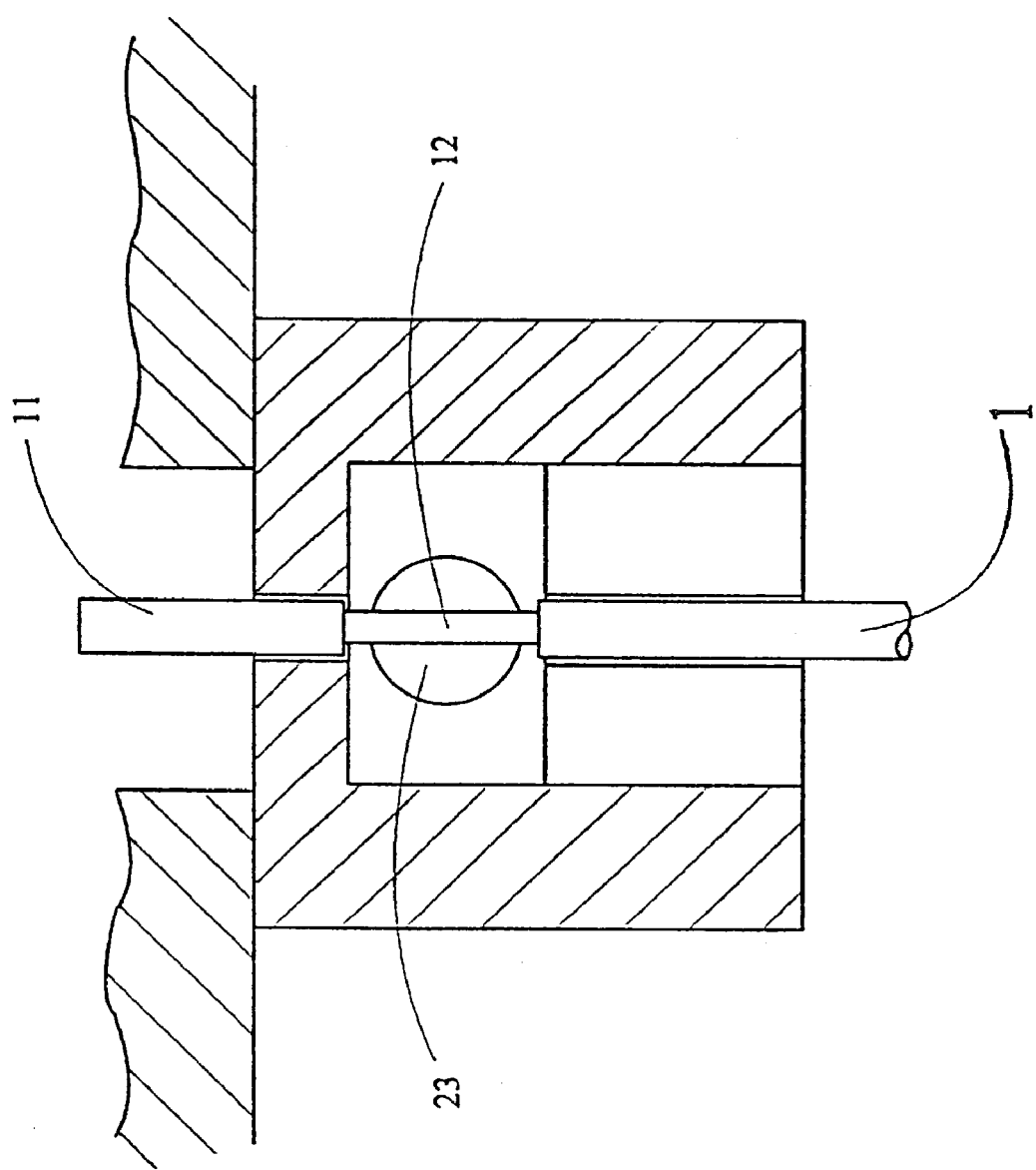
Figure 4:
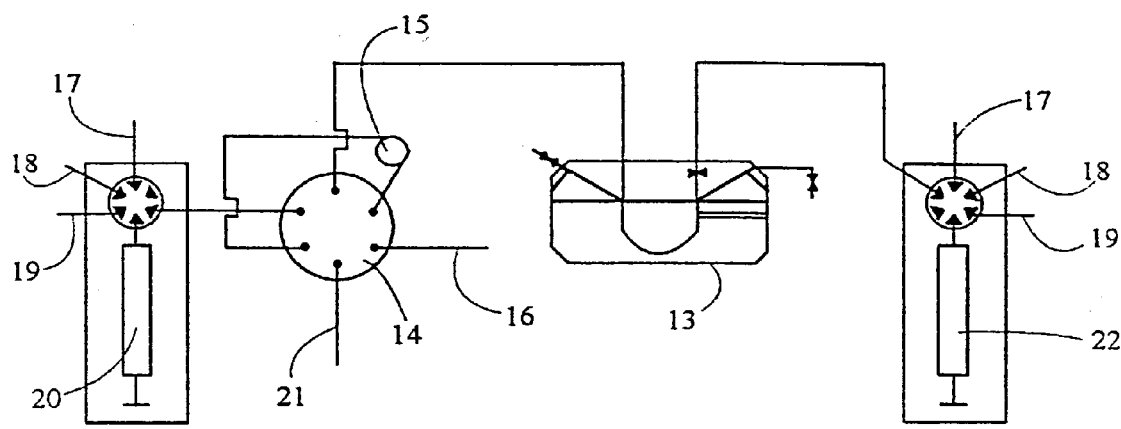
Figure 5:
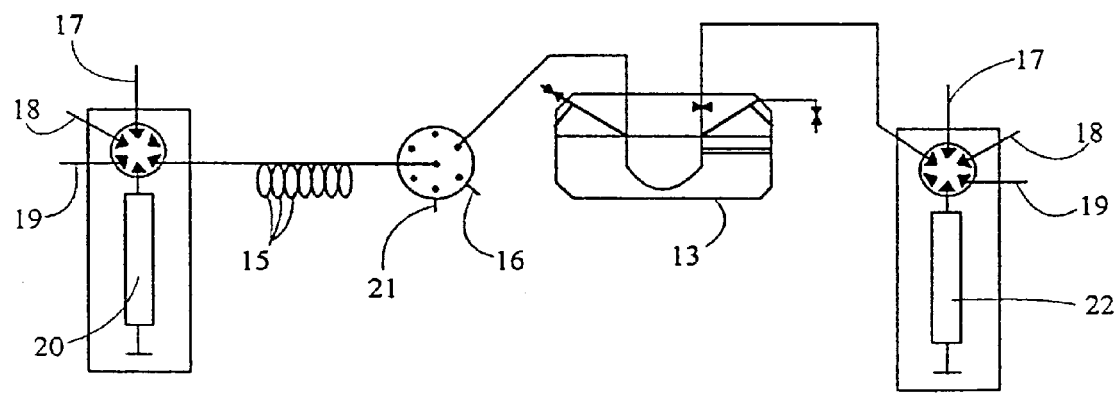
Figure 6:
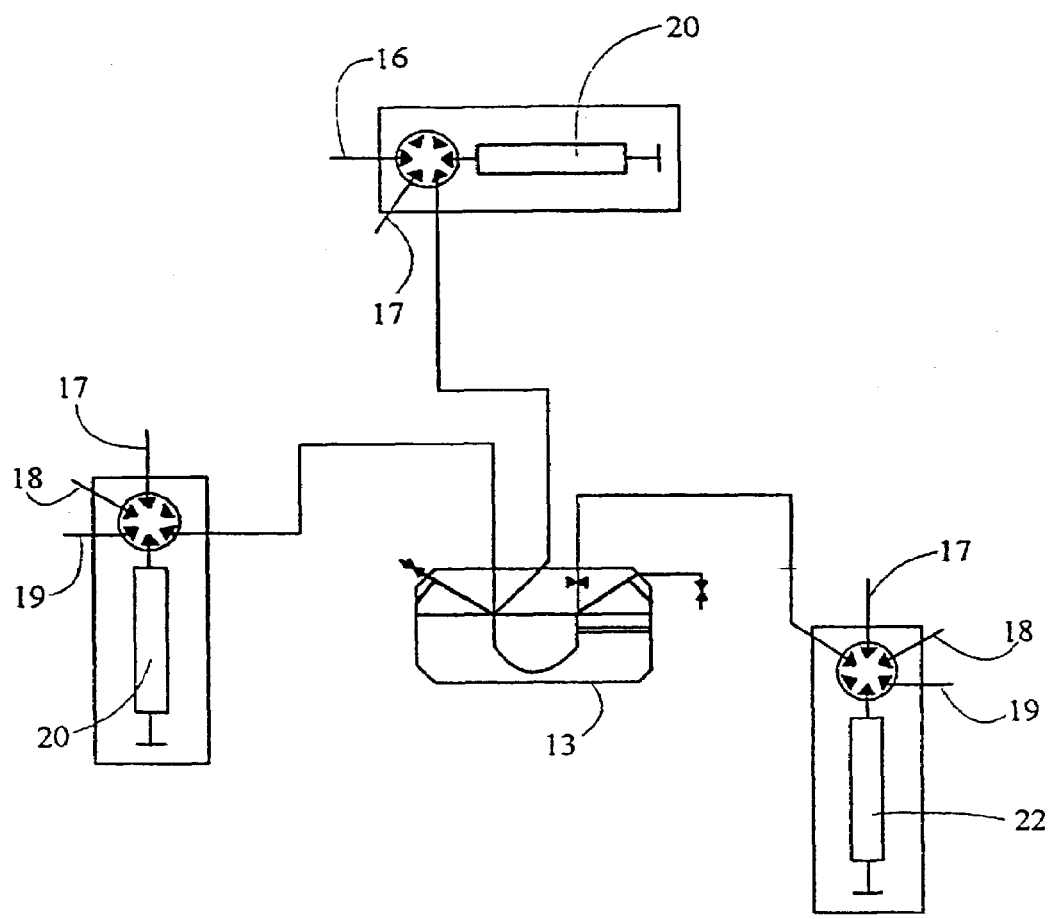

The invention is described below in greater detail, with reference to the accompanying drawings, wherein FIG. 1 depicts a detail of the capillary electrophoresis apparatus according to one embodiment of the invention, FIG. 2 depicts a detail of the capillary electrophoresis apparatus according to another embodiment of the invention, FIGS. 3a and 3b depict a method for focusing the capillary for detection according to one embodiment of the invention, FIG. 4 depicts the apparatus according to the first embodiment of the invention, FIG. 5 depicts the apparatus according to the second embodiment of the invention, FIG. 6 depicts the apparatus according to the third embodiment of the invention.

DETAILED DESCRIPTION

FIGS. 1 and 2 depict details of the capillary electrophoresis apparatuses according to certain embodiments of the invention. The ends of the separation capillary 1 are placed in expansions 5 and 6 continuing from the lower ends of narrow ducts 2 and 3 intended for feeding in various solutions and serving as capillaries. The diameter of the expansions is preferably approx. 1-10 mm. These expansions 5 and 6 continue as waste ducts W1 and W2 to waste containers. The inner diameter of the capillary ducts 2 and 3 is preferably 0.02-1.0 mm and more preferably 0.1-0.5 mm. The electrolyte solution to be used as the background solution flows from containers (not shown in the figures) via these capillary ducts 2 and 3 slowly past both separation-capillary 1 ends towards current electrodes E located in the waste ducts W1 and W2 and connected to a source of voltage, and finally exits the system via the waste ducts to waste containers 7 and 8 (FIG. 2). The waste containers are located at a distance from the ends of the separation capillary 1, and the electrodes E are preferably located at the downstream ends of the waste ducts W1 and W2, whereby the passage of the electrolysis products formed on the electrodes to the separation capillary is prevented, for example owing to the long and spacious waste duct. The flow rate is adjusted in such a manner that the required conditions in the separation capillary 1 are retained and additionally the passage of the electrolysis products of the electrodes to the separation capillary is prevented.

The feeding end 9 of the separation capillary 1 is placed at a height H1 which is the distance from the bottom of the expansion 5 to the junction of the expansion 5 walls substantially parallel to the separation capillary 1 and the expansion 5 walls substantially divergent to the separation capillary 1. The exit end 10 of the separation capillary 1 for its part is located at a height H2 which is in FIG. 1 approx. 20% and in FIG. 2 approx. 70% of the location height H1 of the feeding end 9 of the capillary 1.

The upper part of the expansion 5 may be of any desired shape, for example, spherically symmetrical, conically symmetrical or horn symmetrical.

The feed solution flowing from the solution containers can be replaced independently with the help of pumps, and the flow rates of the various feed solutions can be controlled independently. After an electrophoresis run has been completed, the washing and balancing solutions located in any of the containers can be pumped through the capillary system. A pump can also be installed in a waste duct W2, in which case it works according to the suction principle. In this case, in the figures, instead of pumps it is possible to use valves, and the suction is produced by means of a suction pump. The number of pumps and valves is elective, and it can be selected according to the application used. If a high precision of the flow rate is not required, the pumps may also be entirely replaced with valves and the flow can be produced by gravity or by means of vacuum or overpressure prevailing in the solution vessels. Various embodiments of the method according to the invention with respect to the feeding in of the various solutions are shown in greater detail in FIGS. 4-6.

Substantially in the vicinity of the exit end of the separation capillary 1 there is placed a detector 4, by means of which the particles separated in the capillary are detected. The detection can be carried out, for example, on the basis of the absorbance of the sample. The operation of the entire apparatus can be controlled by means of a microprocessor.

A pump may also be installed in a waste duct W2, in which case it operates according to the suction principle. In this case, valves can be used instead of feeding pumps, and the suction is produced by means of the suction pump in the waste duct. The number of pumps and valves is elective, and it can be selected according to the application used. If a high precision of the flow rate is not required, the pumps may also be entirely replaced by valves and the flow can be produced by gravity or by means of vacuum or overpressure prevailing in the solution vessels.

By the use of suitable pumps and valves, a closed or open capillary electrophoresis can be carried out or a pre-calculated flow rate in the capillary can be produced. With the apparatus according to the invention it is also possible to run various chemical gradients and pulses from either end of the separation capillary during a run.

If the sample solution is fed in by pumping while the electric field is on, a controllable amount of the sample travels into the separation capillary 1. The amount of the sample to be injected is determined by controlling the pumping time, the electric field and the electro-osmotic flow rate.

Electro-osmotic flow can be prevented entirely by closing the detector 4 side of the duct system. Thus it is possible to select a purely hydrodynamic feeding in of a sample by injecting the sample by pumping, or electrokinetic injection by means of the electric field. By a variation of the various parameters, injection type, electric field and hydrodynamic flow, it is possible with the apparatus according to the invention easily to produce several different methods of injection.

FIGS. 3a and 3b depict a method for focusing the capillary for detection according to one embodiment of the invention. FIG. 3b shows a section through B-B in FIG. 3a. The figures show a separation capillary 1, which is secured to standard pieces 11 and 12, which are attached to each other. The separation capillary 1 is focused on the detection area 23 by means of a focusing piece 25. The focusing piece 25 is guided by a spring 26. By means of the focusing piece 25, a ray of light, or the like, used in the detection, can be focused on the separation capillary 1 in a standardized manner.

FIG. 4 depicts the apparatus according to the first embodiment of the invention. The apparatus has a capillary electrophoresis unit 13, on the feed side of which there is connected as a sample feeding system a selection valve 14. To the selection valve there is, in turn, connected a sample loop 15, made of some suitable, preferably insulating, material. A sample from the process is fed into the selection valve 14 via a duct 16, there being between this duct and the process preferably one or more sample collectors in series. It is possible to pre-treat the sample before its being fed to the sample collector or thereafter, for example, to filter and/or dilute it.

The sample collectors may be made from, for example, steel, polyetherether ketone (PEEK), silicon, or some other inactive material. The structures transporting the solutions, for their part, may be tubes or grooves machined in the material. The materials used may be, for example, glass, silicon, various polymers, or metals.

To the selection valve 14 there are also fed the electrolyte and various solutions, such as washing and balancing solutions, via ducts 17, 18 and 19, respectively, which ducts communicate with the respective solution containers. A pump 20 is available for the feeding in of the electrolyte and the solutions. In addition, it is possible to connect a waste duct 21 to the selection valve 14. There are thus available pumps for the transporting of all the liquids, either injection pumps or suction pumps, which fulfill the requirements set by the flow rate variations and the pressure variations.

Through the selection valve it is thus possible to feed in a constant volume of a sample or of some other solution by means of the sample loop 15. Through the selection valve it is also possible to feed solutions into the capillary electrophoresis directly, without a sample loop. The sample loop has thus the advantage that by means thereof it is possible to feed in a constant volume of the sample, regardless of the viscosity of the sample. By means of the sample loop, there is also achieved insulation from the ground potential, necessary in capillary electrophoresis, as well as insulation of the sample from the capillary electrophoresis unit 13, at the sample collection stage. It is clear that continuous through-flow is also possible.

Furthermore, on the exit side of the capillary electrophoresis unit 13 there is linked a liquid treatment system having a pump 22 and connections for feeding in the electrolyte and various liquids via ducts 17, 18 and 19.

In the first embodiment described it is possible to use the same pressure at both ends of the separation capillary, or a small pressure difference, in which case it is possible to manipulate the passage of the sample into the capillary. The flow rates of the sample-feeding system and the liquid-treatment system, and the amounts and pressures of the solutions can all be controlled together or separately.

FIG. 5 shows the apparatus according to the second embodiment of the method. This embodiment has seven parallel sample loops 15 located between the selection valve and the feeding system for the electrolyte and for solutions. The sample, for its part, is fed from the selection valve 14 directly into the capillary electrophoresis unit 13. In other respects the apparatus is similar to the apparatus shown in FIG. 4.

With the apparatus according to the second embodiment it is possible, with the help of the parallel sample loops, to construct solution queues of the various solutions, the queues being fed into the capillary electrophoresis unit. It is also possible to equip the exit end of the separation capillary with such a sample loop series.

FIG. 6 shows the apparatus according to the third embodiment of the invention. The apparatus has a capillary electrophoresis unit 13, on the feed side of which there is linked a sample-feeding system into which the sample is fed from the process via duct 16, there being between this duct and the process preferably one or more sample collectors in series. It is also possible to feed into the sample-feeding system an electrolyte via duct 17. On the feed side of the unit 13 there is also connected a liquid-treatment system similar to that in FIGS. 4 and 5, by means of which, for example, electrolyte 17 can be fed into the unit. The liquid streams from the sample-feeding system and the liquid-treatment system are preferably combined at a point as close as possible to the feeding end of the separation capillary. The liquid-treatment system of the apparatus is preferably similar to that in the apparatus shown in FIG. 4.

The method and apparatus according to the invention thus have several different embodiments. When so desired, any of the embodiments and run conditions can be selected and, when necessary, be modified during the run.

When the apparatus according to the invention is used it is easy to select and implement the initial and limit conditions for various electrophoresis applications. Furthermore, it is possible to use combined methods by changing the limit conditions during an electrophoresis run.

Certain applications of the invention are presented above. The invention is, of course, not restricted to the embodiments described above; the principle according to the invention can be varied within the protective scope of the patent claims.

The invention claimed is:

1. A capillary electrophoresis apparatus for on-line analysis of a sample taken from a process, said capillary electrophoresis apparatus having a capillary electrophoresis unit (13) having a feed side and an exit side, said capillary electrophoresis unit (13) comprising:
    a separation capillary (1) having a feeding end (9) and an exit end (10),
    current electrodes (E) connected to a source of voltage, and
    a detector (4) substantially in the vicinity of the exit end (10) of the separation capillary (1),
    the ends of the said separation capillary (1) being located in expansions (5, 6) continuing from the lower ends of capillary ducts (2, 3), which expansions continue as waste ducts (W1, W2) to waste containers, the waste containers being located at a distance from the ends of the separation capillary (1), and the current electrodes (E) being located in the waste ducts (W1, W2),
    wherein on the feed side of the capillary electrophoresis unit (13) the sample is continuously collected via a duct (16) from the process into a sample feeding system and fed into the capillary ducts (2, 3) through the same duct as is a feed solution, and the sample feeding system is one of sample-loop-in-valve system comprising a selection valve (14) connected to a sample loop (15), an introduction system comprising a selection valve (14)

connected to parallel sample loops (15) or an introduction system comprising a syringe, and all solutions on the feed side and exit side of the capillary electrophoresis unit (13) are pumped through the flow ducts, and liquids which flow through the separation capillary (1) are removed on the exit end (10) of the capillary electrophoresis unit (13) by a liquid treatment system.

2. The apparatus according to claim 1, wherein the feeding end (9) of the separation capillary (1) is located substantially at a height H1 which height Hi is the distance from the expansion (5) bottom to the junction of the expansion (5) walls substantially parallel to the separation capillary (1) and the expansion (5) walls substantially divergent to the separation capillary (1).

3. The apparatus according to claim 2, wherein the exit end (10) of the separation capillary (1) is located at a height H2 that is substantially smaller than the placement height H1 of the feeding end (9) of the capillary (1).

4. The apparatus according to claim 3, wherein the exit end (10) of the separation capillary (1) is placed at a height H2 that is 10-85% of the placement height H1 of the feeding end (9) of the capillary (1).

5. The apparatus according to claim 4, wherein the exit end (10) of the separation capillary (1) is placed at a height H2 that is 20-70% of the placement height H1 of the feeding end (9) of the capillary (1).

6. The apparatus according to claim 1, wherein the diameter of the expansions (5, 6) is approximately 1-10 mm.

7. The apparatus according to claim 1, wherein the inner diameter of the capillary ducts (2, 3) and the separation capillary (1) is 0.02-1.0 mm.

8. The apparatus according to claim 7, wherein the inner diameter of the capillary ducts (2, 3) and the separation capillary (1) is 0.1-0.5 mm.

9. The apparatus according to claim 1, wherein flow in the capillary ducts (2, 3) is created by means of gravity or by means of vacuum or overpressure.

10. The apparatus according to claim 1, wherein the sample is fed by means of a selection valve (14).

11. The apparatus according to claim 1, wherein the sample is connected with an electrolyte and optionally other solutions before feeding into the separation capillary (1), and wherein the electrolyte and other optional solutions are removed by means of said liquid treatment system.

12. The apparatus according to claim 1, wherein the current electrodes (E) are located in the vicinity of the downstream ends of the waste ducts (W1, W2).

13. The apparatus according to claim 1, wherein there are seven parallel sample loops.

14. The apparatus according to claim 1, wherein the sample feeding is by an electrokinetic device, by a pressure device or by a hydrodynamic device.

15. The apparatus according to claim 1, wherein the expansion (5) has an upper part with a spherical symmetrical shape, a conically symmetrical shape or a horn symmetrical shape.

16. A capillary electrophoresis apparatus for on-line analysis of a sample taken from a process, said capillary electrophoresis apparatus having a capillary electrophoresis unit (13) having a feed side and an exit side, said capillary electrophoresis unit (13) comprising:

a separation capillary (1) having a feeding end (9) and an exit end (10), current electrodes (E) connected to a source of voltage, and a detector (4) substantially in the vicinity of the exit end (10) of the separation capillary (1), the ends of the said separation capillary (1) being located in expansions (5, 6) continuing from the lower ends of capillary ducts (2, 3), which expansions continue as waste ducts (W1, W2) to waste containers, the waste containers being located at a distance from the ends of the separation capillary (1), and the current electrodes (E) being located in the waste ducts (W1, W2), wherein on the feed side of the capillary electrophoresis unit (13) the sample is continuously collected via a duct (16) from the process into a sample feeding system, which is a sample-loop-in-valve system comprising a selection valve (14) connected to a sample loop (15) and fed into the capillary ducts (2, 3) through the same duct as is a feed solution, wherein all solutions on the feed side and exit side of the capillary electrophoresis unit (13) are pumped through the flow ducts, and liquids which flow through the separation capillary (1) are removed on the exit end (10) of the capillary electrophoresis unit (13) by a liquid treatment system.

17. A capillary electrophoresis apparatus for on-line analysis of a sample taken from a process, said capillary electrophoresis apparatus having a capillary electrophoresis unit (13) having a feed side and an exit side, said capillary electrophoresis unit (13) comprising:

a separation capillary (1) having a feeding end (9) and an exit end (10), current electrodes (E) connected to a source of voltage, and a detector (4) substantially in the vicinity of the exit end (10) of the separation capillary (1), the ends of the said separation capillary (1) being located in expansions (5, 6) continuing from the lower ends of capillary ducts (2, 3), which expansions continue as waste ducts (W1, W2) to waste containers, the waste containers being located at a distance from the ends of the separation capillary (1), and the current electrodes (E) being located in the waste ducts (W1, W2), wherein on the feed side of the capillary electrophoresis unit (13) the sample is continuously collected via a duct (16) from the process into a sample feeding system, which is an introduction system comprising a selection valve (14) connected to parallel sample loops (15) and fed into the capillary ducts (2, 3) through the same duct as is a feed solution, wherein all solutions on the feed side and exit side of the capillary electrophoresis unit (13) are pumped through the flow ducts, and liquids which flow through the separation capillary (1) are removed on the exit end (10) of the capillary electrophoresis unit (13) by a liquid treatment system.

18. The apparatus according to claim 17, wherein there are seven parallel sample loops.

19. A capillary electrophoresis apparatus for on-line analysis of a sample taken from a process, said capillary electrophoresis apparatus having a capillary electrophoresis unit (13) having a feed side and an exit side, said capillary electrophoresis unit (13) comprising:

a separation capillary (1) having a feeding end (9) and an exit end (10), current electrodes (E) connected to a source of voltage, and a detector (4) substantially in the vicinity of the exit end (10) of the separation capillary (1), the ends of the said separation capillary (1) being located in expansions (5, 6) continuing from the lower ends of capillary ducts (2, 3), which expansions continue as waste ducts (W1, W2) to waste containers, the waste containers being located at a distance from the ends of the separation capillary (1), and the current electrodes (E) being located in the waste ducts (W1, W2), wherein on the feed side of the capillary electrophoresis unit (13) the sample is continuously collected via a duct (16) from the process into a sample feeding system, which is an introduction system comprising a syringe, and fed into the capillary ducts (2, 3) through the same duct as is a feed solution, wherein all solutions on the feed side and exit side of the capillary electrophoresis unit (13) are pumped through the flow ducts, and liquids which flow through the separation capillary (1) are removed on the exit end (10) of the capillary electrophoresis unit (13) by a liquid treatment system.

\* \* \* \* \*